US012485035B1

(12) United States Patent
Clingan et al.

(10) Patent No.: US 12,485,035 B1
(45) Date of Patent: Dec. 2, 2025

(54) OSTOMY APPARATUSES AND METHODS OF USE

(71) Applicants: Rodney Clingan, Tulsa, OK (US); Robert Adams, Tulsa, OK (US)

(72) Inventors: Rodney Clingan, Tulsa, OK (US); Robert Adams, Tulsa, OK (US)

( * ) Notice: Subject to any disclaimer, the term of this patent is extended or adjusted under 35 U.S.C. 154(b) by 724 days.

(21) Appl. No.: 17/734,779

(22) Filed: May 2, 2022

(51) Int. Cl.
*A61F 5/448* (2006.01)
*A61F 5/44* (2006.01)
*A61F 5/445* (2006.01)

(52) U.S. Cl.
CPC ...... *A61F 5/448* (2013.01); *A61F 2005/4486* (2013.01)

(58) Field of Classification Search
CPC ... A61F 5/448; A61F 2005/4486; A61F 5/445
See application file for complete search history.

(56) References Cited

U.S. PATENT DOCUMENTS 3,565,073 A * 2/1971 Giesy ...................... A61F 5/449 623/66.1
3,952,726 A * 4/1976 Hennig ..................... A61F 5/44 600/32
4,154,226 A * 5/1979 Hennig ................. A61F 2/0009 600/32
4,205,678 A * 6/1980 Adair ...................... A61F 5/448 604/343
4,210,132 A * 7/1980 Perlin ................... A61F 2/0018 600/32
4,636,205 A * 1/1987 Steer ....................... A61F 5/448 604/338
4,904,256 A * 2/1990 Yamaguchi ........... A61F 2/0018 128/DIG. 25
5,273,529 A * 12/1993 Idowu ................. A61J 15/0065 604/537
5,330,455 A * 7/1994 McKay ................... A61F 5/448 604/339
5,813,976 A * 9/1998 Filipi ..................... A61B 90/50 600/102
6,030,392 A * 2/2000 Dakov ............... A61B 17/1152 606/151
7,241,300 B2 * 7/2007 Sharkawy .......... A61B 17/0057 623/1.36
7,780,641 B2 * 8/2010 Ferko ...................... A61F 5/445 604/335
7,938,841 B2 * 5/2011 Sharkawy .............. A61B 17/11 606/153
8,518,062 B2 * 8/2013 Cole .................. A61B 17/0057 606/153
8,764,717 B2 * 7/2014 Willoughby ............ A61F 5/445 604/338
8,858,520 B2 * 10/2014 Gregory .................. A61F 5/445 604/346

(Continued)

*Primary Examiner* — Guy K Townsend
(74) *Attorney, Agent, or Firm* — Lexigent LLC

(57) ABSTRACT

Ostomy apparatuses and methods of use are disclosed herein. An example apparatus can include an ostomy interface configured to be inserted into a stoma of a patient, the ostomy interface being shaped so as to prevent disassociation of the ostomy interface from the stoma, the ostomy interface having an annular upper flange; and a securement interface that is configured to lockingly mate with the annular upper flange of the ostomy interface and couple an ostomy bag to the ostomy interface.

8 Claims, 8 Drawing Sheets

(56) References Cited

U.S. PATENT DOCUMENTS

| | | | | |
|---|---|---|---|---|
| 8,998,867 | B2 * | 4/2015 | Sabeti | A61F 5/4405 604/335 |
| 10,413,399 | B2 * | 9/2019 | Blom | A61F 2/20 |
| 11,129,744 | B2 * | 9/2021 | Granet | A61F 5/448 |
| 2007/0010834 | A1 * | 1/2007 | Sharkawy | A61B 17/11 606/153 |
| 2008/0312614 | A1 * | 12/2008 | Ferko | A61F 5/445 604/332 |
| 2011/0040231 | A1 * | 2/2011 | Gregory | A61F 5/445 604/8 |
| 2018/0098876 | A1 * | 4/2018 | Wright | A61F 5/448 |

* cited by examiner

OSTOMY APPARATUSES AND METHODS OF USE

CROSS-REFERENCE TO RELATED APPLICATION(S)

N/A.

TECHNICAL FIELD

The present disclosure pertains to ostomy apparatuses and methods of use, such as for colostomies, ileostomies, and so forth.

SUMMARY

According to some embodiments, the present disclosure is directed to an apparatus comprising an enterostomy interface configured to be inserted into a stoma of a patient and associated with an enterostomy of the patient, the enterostomy interface being shaped so as to prevent disassociation of the enterostomy interface with the stoma, the enterostomy interface comprising an annular upper flange; and a securement interface that is configured to lockingly mate with the annular upper flange of the enterostomy interface and couple an ostomy bag to the enterostomy interface.

In one embodiment, the apparatus further comprises a sleeve that is configured to cover at least a portion of the annular upper flange. In one embodiment, the apparatus further comprises a seal placed into a seal groove located within a perimeter of an upper surface of the annular upper flange, the seal being positioned between the annular upper flange and the securement interface.

In one embodiment, the securement interface comprises an upper ring and a lower ring, a further wherein the ostomy bag is secured to the upper ring and the lower ring. In one embodiment, a lower ring of the securement interface is configured to threadingly engage with the annular upper flange.

In one embodiment, the annular upper flange is threaded and comprises a detent slot. In one embodiment, the lower ring further comprises a resilient mechanical detent comprising a protrusion coupled to an actuator, the protrusion drops into a detent slot of the annular upper flange when the lower ring of the securement interface is threadingly engaged with the annular upper flange.

In one embodiment, the actuator is configured to be lifted to remove the protrusion from the detent slot when disengaging the securement interface from the annular upper flange.

According to some embodiments, the present disclosure is directed to an apparatus comprising: an enterostomy interface that is configured to be partially inserted into a stoma opening and beneath the skin of a patient, the apparatus comprising: a flared lower flange that is located underneath the skin; and an annular upper flange that is located above the skin, such that the skin is located between the flared lower flange and the annular upper flange when the enterostomy interface extends through the stoma.

In one embodiment, the apparatus includes a groove in an upper surface of the annular upper flange. In one embodiment, the apparatus includes a seal that is placed into the groove. In one embodiment, the annular upper flange is adjustable to compress against an outer surface of the flared lower flange.

In one embodiment, the apparatus includes ostomy bag an ostomy bag having a securement interface that is configured to lockingly mate with the annular upper flange of the enterostomy interface. In one embodiment, the annular upper flange is threaded and comprises a detent slot.

In one embodiment, the securement interface comprises a resilient mechanical detent comprising a protrusion coupled to an actuator, the protrusion drops into a detent slot of the annular upper flange when the lower ring of the securement interface is threadingly engaged with the annular upper flange. In one embodiment, the apparatus includes a graft material covering at least a portion of the flared lower flange.

According to some embodiments, the present disclosure is directed to an apparatus comprising: ostomy bag an ostomy bag appliance having a securement interface comprising a lower ring; an enterostomy interface that is configured to be at least partially inserted into a stoma opening and beneath the skin of a patient, the enterostomy interface comprising an annular upper flange that sits above the skin; and an O-ring positioned between the lower ring and the annular upper flange, the O-ring creating a seal between the ostomy bag and the enterostomy interface when the lower ring is coupled with the annular upper flange.

In one embodiment, the securement interface comprises a resilient mechanical detent comprising a protrusion coupled to an actuator, the protrusion drops into a detent slot of the annular upper flange when the lower ring of the securement interface is threadingly engaged with the annular upper flange. In one embodiment, an edge of the ostomy bag is sealed between the lower ring and an upper ring of the securement interface.

According to some embodiments, an apparatus may include a first interface placed into a stoma of a patient, the first interface being configured to house or serve as conduit to a terminal end of a bowel of a patient; and a second interface associated with ostomy bag an ostomy bag, the second interface being used to releaseably secure the second interface with the first interface.

In one embodiment, the apparatus comprises an O-ring positioned between the lower ring and the annular upper flange, the O-ring creating a seal between the first interface and the second interface. In one embodiment, the second interface comprises: an armature; a protrusion on a terminal end of the armature; and wherein the armature is resiliently biased and configured to pivot to move the protrusion up and down.

In one embodiment, the first interface comprises a detent track, the protrusion being compressed against the detent track and moving the armature in response to the second interface being threaded onto the first interface. In one embodiment, the armature pushes the protrusion into a detent slot of the first interface when the protrusion and the detent slot are aligned.

BRIEF DESCRIPTION OF THE DRAWINGS

The detailed description is set forth with reference to the accompanying drawings. The use of the same reference numerals may indicate similar or identical items. Various embodiments may utilize elements and/or components other than those illustrated in the drawings, and some elements and/or components may not be present in various embodiments. Elements and/or components in the figures are not necessarily drawn to scale. Throughout this disclosure, depending on the context, singular and plural terminology may be used interchangeably.

DETAILED DESCRIPTION

Overview

Figure 1:
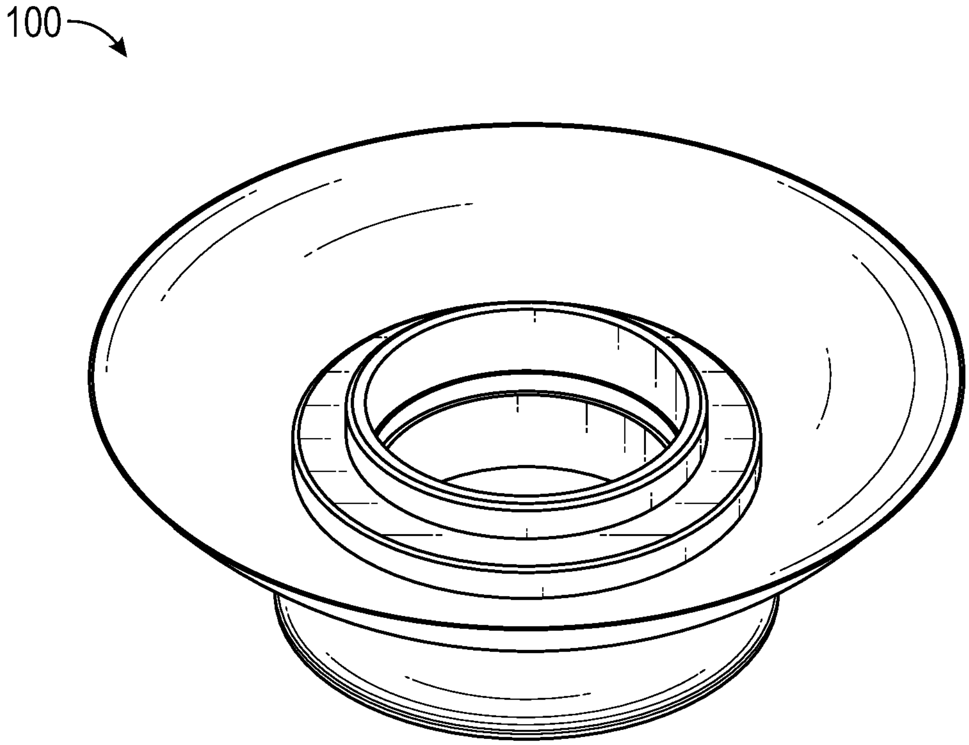
FIG. 1 is a perspective view of an example colostomy apparatus of the present disclosure.

For context, an enterostomy is a temporary or permanent enteric diversion that allows contents of the large or small bowel to be collected outside the body. An enterostomy involves the creation of a stoma or aperture through the skin of the patient. A terminal end of the bowel (e.g., enterostomy) is pulled through and sutured to the stoma. The terminal end of the bowel may protrude through the stoma a specified distance. An enterostomy can include, for example, a colostomy (large bowl), an ileostomy (small bowel), appendicostomy, urostomy, percutaneous endoscopic gastrostomy, and the like. Examples herein may refer to a terminal end of a bowel or "enterostomy", but the present disclosure is not so limited and can be extended to use with other surgically created ports from other bodily structures.

To collect waste, an ostomy bag can be attached to the patient around the stoma. With respect to both ileostomies and colostomies, because the terminal end of the bowel protrudes, it can empty waste into the ostomy bag. Common methods for attaching the ostomy bag include, but are not limited to, the use of adhesives, where an interface or opening of the ostomy bag apparatus adheres to the skin around the stoma. This type of adherence can result in skin irritation and/or the creation of skin lesions, especially when the ostomy bag is removed. Also, even when installed properly, bodily waste products or skin reaction may result in leakage from the apparatus due to loss of adherence. In some instances, the interface of the ostomy bag may attach to a separate enterostomy patch that is affixed to the skin, but this is also typically accomplished using an adhesive. Additionally, the terminal end of the bowel that extends through the stoma is left exposed when not covered by ostomy bag an ostomy bag or other temporary covering.

The present disclosure pertains to ostomy apparatuses and methods of use that do not require the use of skin irritants such as adhesives to mate an ostomy bag with a stoma of a patient. An example enterostomy apparatus includes an enterostomy interface and a securement interface that couples an ostomy bag to the enterostomy interface. The enterostomy interface can be surgically implanted at least partially (or entirely) underneath the skin of the patient. The enterostomy interface is shaped so as to prevent or reduce a likelihood of the enterostomy interface being pulled out of (or otherwise decoupled from) the patient. The enterostomy interface is hollow and includes a pathway for the patient's bowel. In some embodiments, the enterostomy interface is lined internally and externally with a graft material, which allows the skin and/or bowel to fuse with the enterostomy interface. The terminal end of the bowel is covered by and hidden within the enterostomy interface. Thus, the enterostomy interface protects the terminal end of the bowel that protrudes from the stoma from damage. This also enhances the patient's quality of life as they do not have to view the terminal end of the bowel.

The securement interface can be coupled with an enterostomy bag in some embodiments. In other embodiments, the enterostomy bag is integrated into the securement interface. In various embodiments, the enterostomy interface and securement interface are configured to releasably lock together. An O-ring, gasket, or another similar sealing member can be placed between the mating surfaces of the enterostomy interface and the securement interface to prevent waste products from leaking.

Illustrative Embodiments

Figure 2:
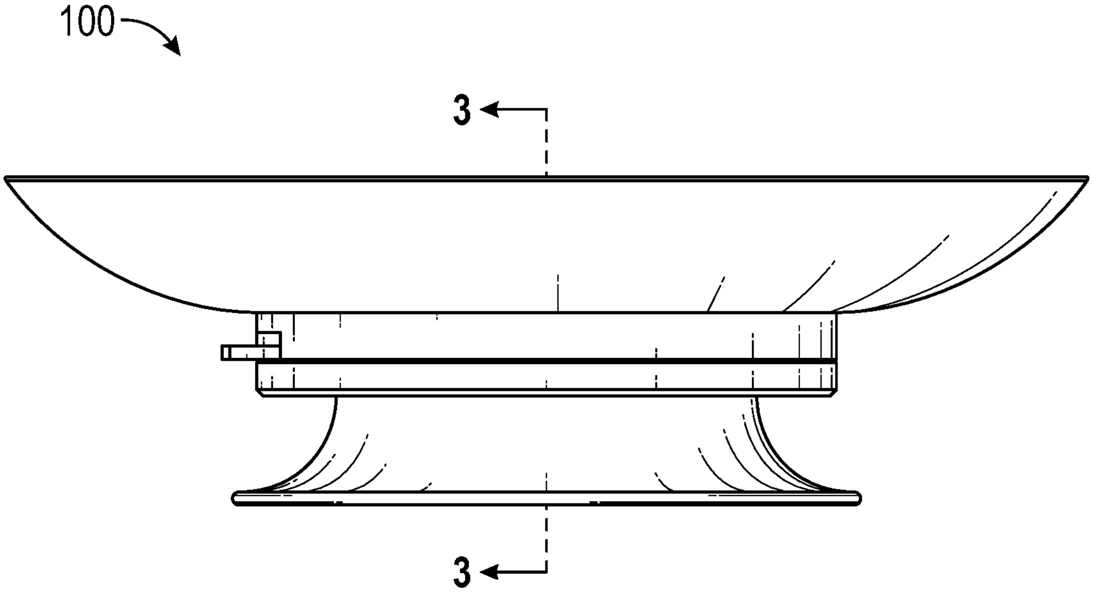
FIG. 2 is an elevation view of the colostomy apparatus of FIG. 1.

FIG. 1 is a perspective view of an example colostomy apparatus (hereinafter apparatus 100) of the present disclosure, which is also shown in a front elevation view in FIG. 2. The apparatus 100 include an enterostomy interface 102 (also may be referred to as a first interface), a securement interface 104 (also may be referred to as a second interface), and an ostomy bag 106, a seal 108, and a graft covering 110. These parts are also shown in cross-section in FIG. 3 and in an exploded perspective view in FIG. 4.

Figure 3:
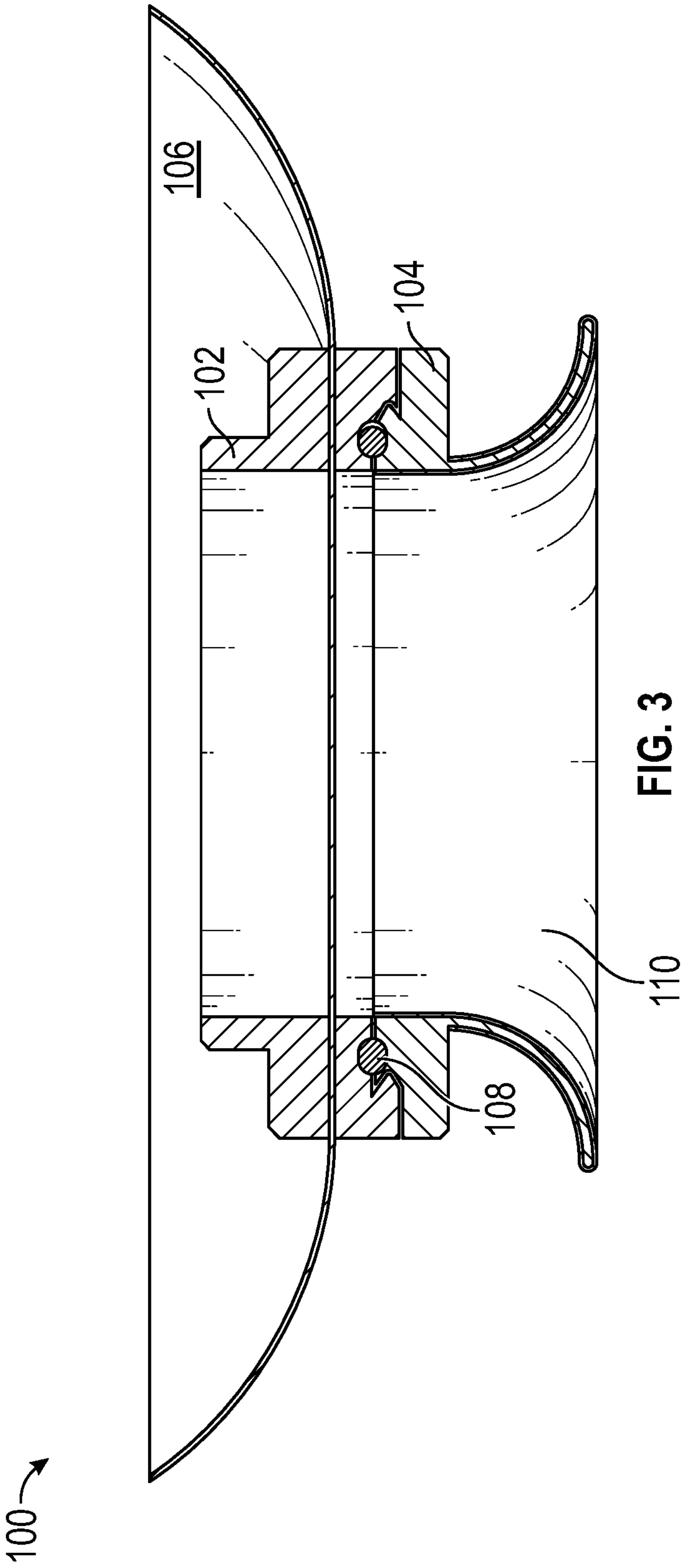
FIG. 3 is a cross-section view taken along section line A-A of FIG. 2.
Figure 4:
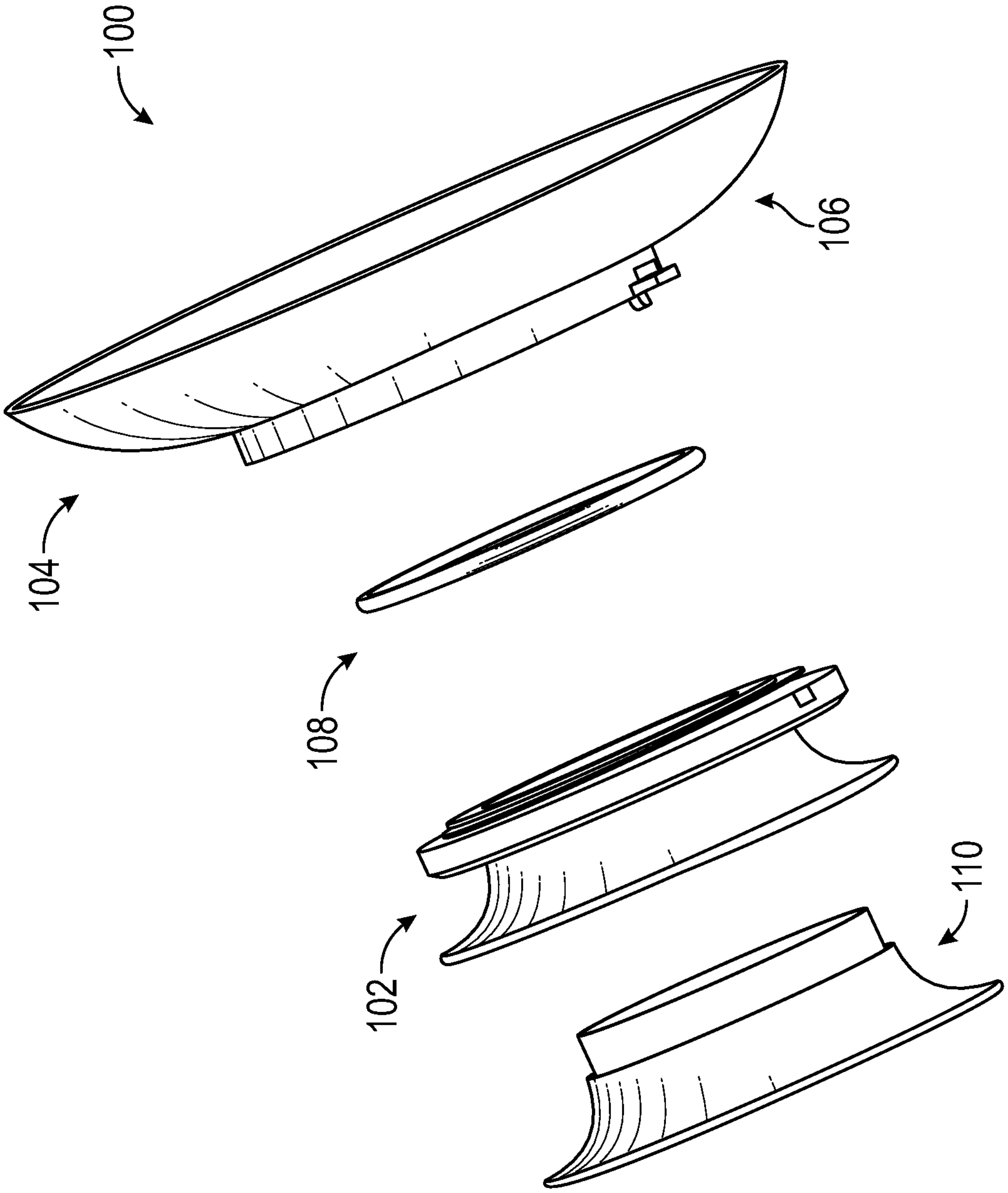
FIG. 4 is an exploded perspective view of the colostomy apparatus of FIG. 1.
Figure 5:
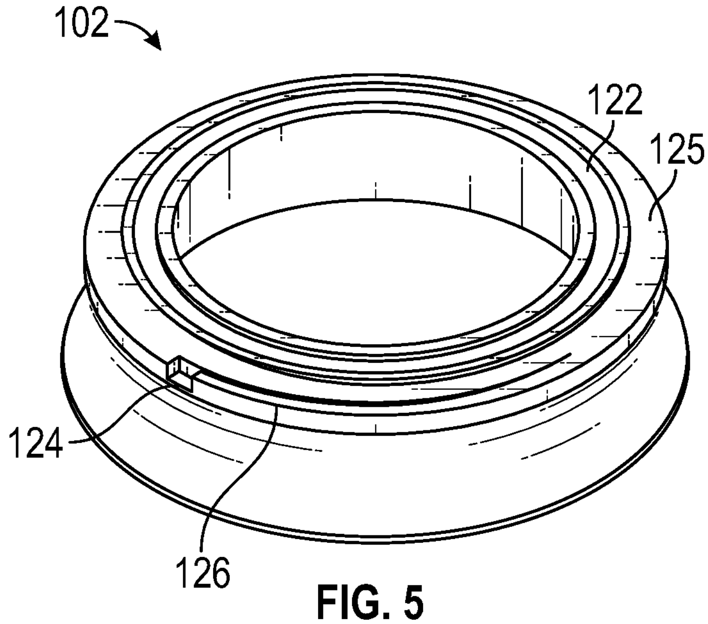
FIG. 5 is a perspective view of an example enterostomy interface.
Figure 6:
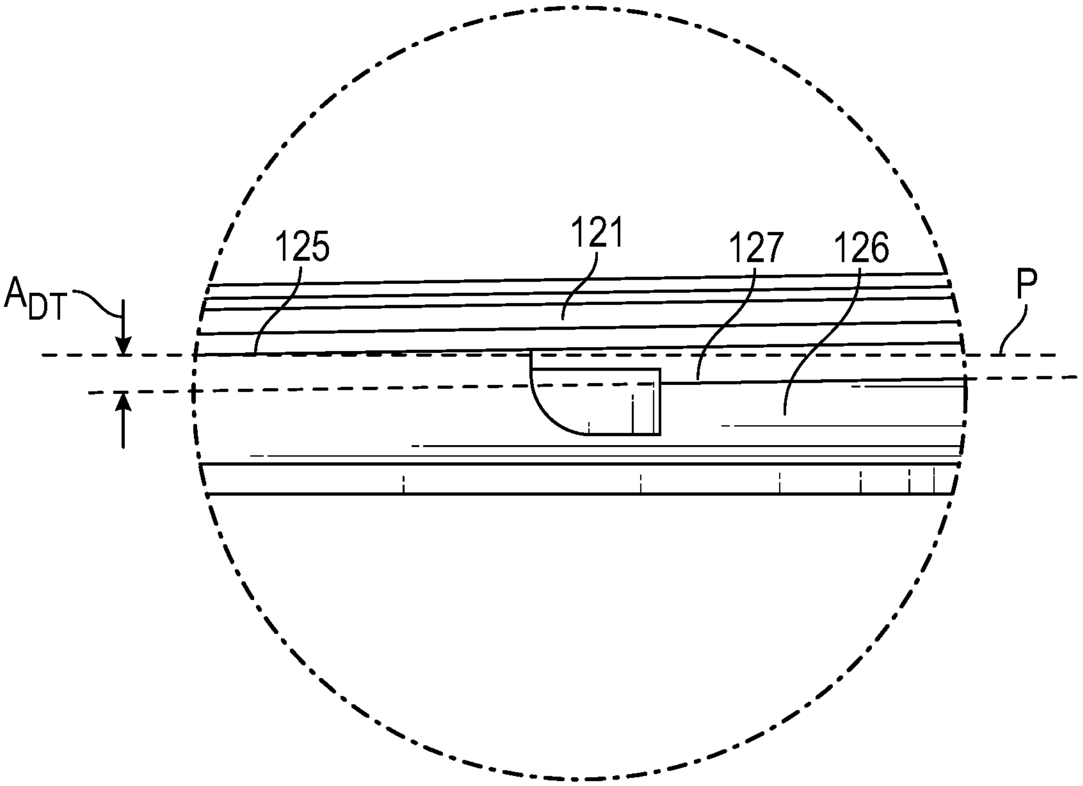
FIG. 6 is a close-up view of a portion of the example enterostomy interface.
Figure 7:
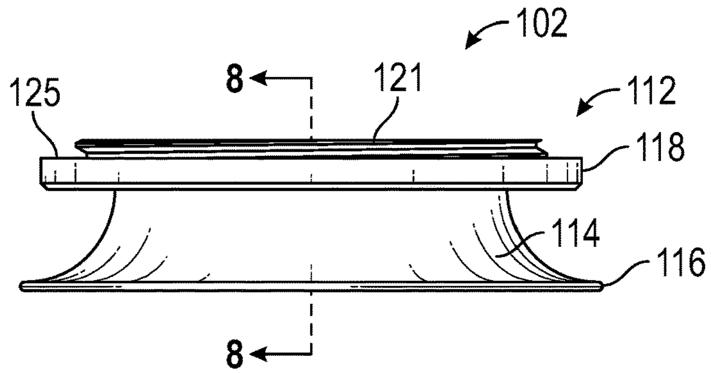
FIG. 7 is an elevation view of an example enterostomy interface.
Figure 8:
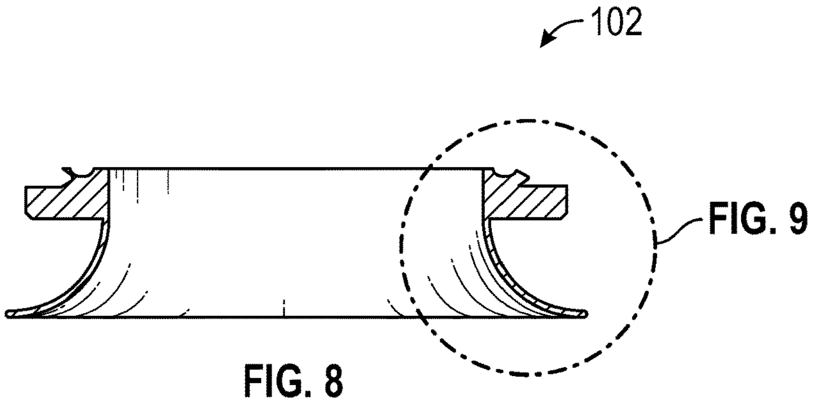
FIG. 8 is a cross-sectional view taken along section line B-B of FIG. 7.
Figure 9:
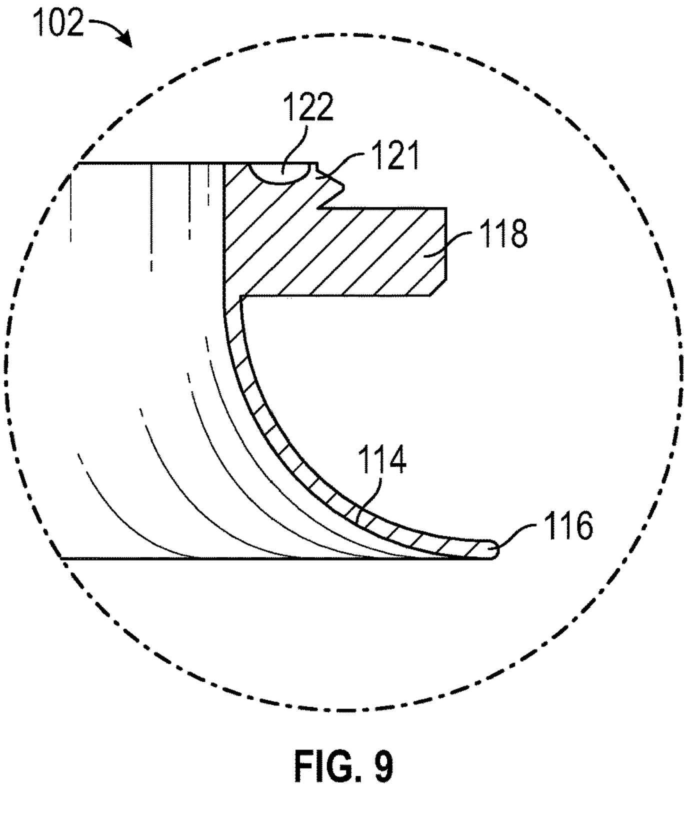
FIG. 9 is a close-up, partial cross-sectional view taken along the sectional line of FIG. 8.
Figure 10:
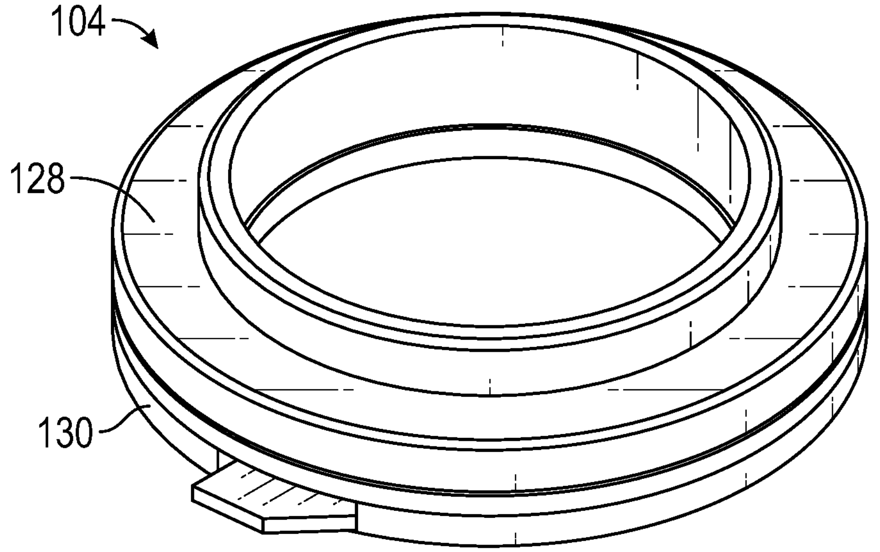
FIG. 10 is a perspective view of an example securement interface.
Figure 11:
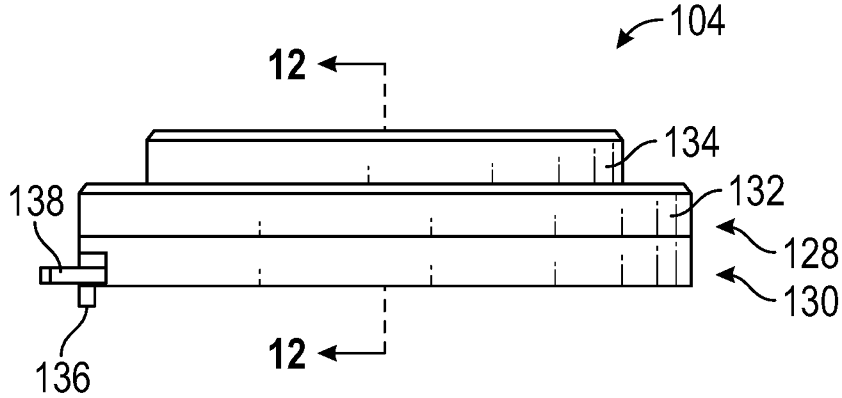
FIG. 11 is an elevation view of an example securement interface.
Figure 12:
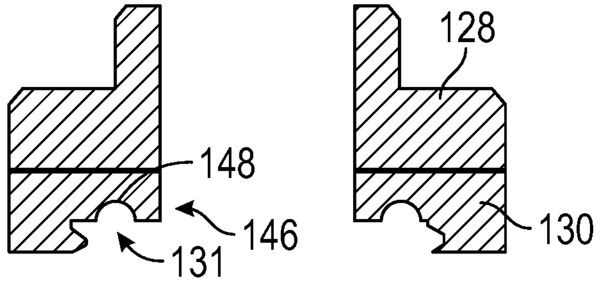
FIG. 12 is a cross-section view taken along section line H-H of FIG. 11.
Figure 13:
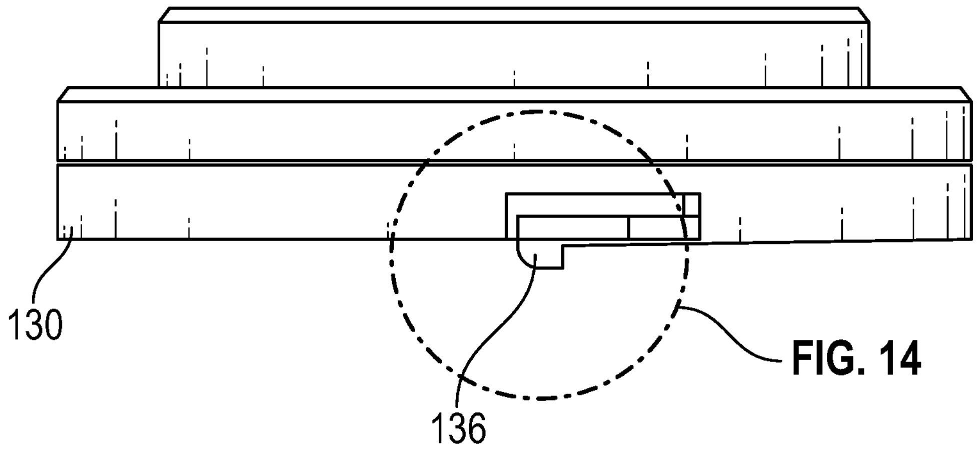
FIG. 13 is an elevation view of an example securement interface, illustrating a resilient mechanical detent.
Figure 14:
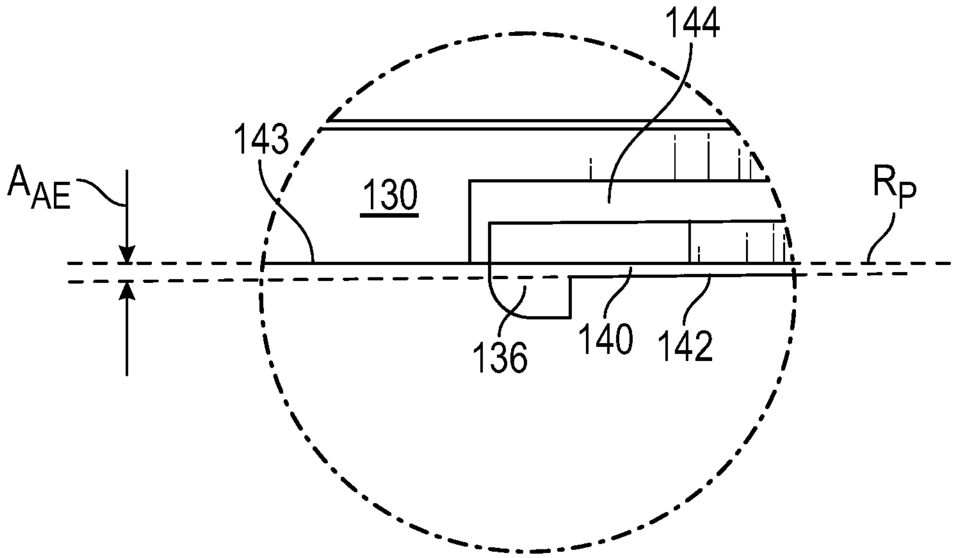
FIG. 14 is a close-up view of the resilient mechanical detent.

Referring specifically to FIG. 3, when assembled, the graft covering 110 is inserted into the enterostomy interface 102, and the ostomy bag 106 is secured to the enterostomy interface 102 by way of the securement interface 104. The seal 108 is placed between the enterostomy interface 102 and the securement interface 104. In some embodiments, the graft covering 110 can be omitted or replaced with a suitable substitute material.

Referring now to FIGS. 5-9 collectively, which illustrate the enterostomy interface 102. The enterostomy interface 102 is configured to be inserted into the abdominal wall and serve as a conduit for the enterostomy of the patient. In general, the enterostomy interface 102 is shaped so as to prevent disassociation from the skin or bowel comprising the enterostomy. The enterostomy interface 102 may comprise an annular upper flange 112 and a flared lower flange 114. The flared lower flange 114 extends from a lower end of the annular upper flange 112 and has a sidewall with a concave profile. A terminal end 116 of the flared lower flange 114 has an outer peripheral edge that has a diameter that is greater than a diameter of the annular upper flange 112. in some embodiments. The diameter of the flared lower flange 114 is sized such that when the flared lower flange 114 is inserted into the stoma by a surgeon, the flared lower flange 114 may abut an underside of the skin and subcutaneous tissue around the stoma to prevent the flared lower flange 114 from being pulled out of the patient's abdominal wall/stoma. An example of the apparatus 100 in situ in a patient is illustrated in FIG. 17.

As noted above, the graft covering 110 lines an inner surface of the flared lower flange 114. The graft covering 110 can be integrated to allow for the patient's enterostomy to sutured onto the graft covering 110. Example graft materials can include but are not limited to, Dacron™. Other materials can be used to line the inner surface of the graft covering 110 that would be known to one of ordinary skill in the art with the present disclosure before them. It will be understood that the graft covering 110 is an optional component. An adhesive or other bonding type may be used to secure the graft covering 110 to the inner surface of the flared lower flange 114.

The annular upper flange 112 can comprise a body 118 having a threaded collar 121, a seal groove 122, a detent slot 124, and detent track 126. In some embodiments, the seal groove 122 is recessed into an upper surface of the threaded collar 121. The threaded collar 121 can extend normally or orthogonally to an upper surface 125 of the body 118. In various embodiments, the detent track 126 is fabricated into the upper surface 125 of the body 118 and is placed near an outer peripheral edge of the upper surface 125 of the body 118. The detent track 126 is defined by a track surface 127 that is progressively sloped at an angle $A_{DT}$ relative to a plane P that is coplanar with the upper surface 125. The detent track 126 receives a protrusion of a resilient mechanical detent associated with the securement interface 104, as will be discussed in greater detail herein.

The seal 108 is placed into the seal groove 122 located within a perimeter of an upper surface of the annular upper flange 112. The seal 108 is positioned between the annular upper flange 112 and the securement interface 104 to prevent leakage of waste material there between.

According to some embodiments, the securement interface 104 is configured to lockingly mate with the annular upper flange 112 of the enterostomy interface 102. The securement interface 104 is used to join the ostomy bag 106 to the enterostomy interface 102.

Referring now to FIGS. 10-14, in some embodiments, the securement interface 104 comprises an upper ring 128 and a lower ring 130. A peripheral edge of a hole or opening of the ostomy bag 106 is sandwiched between the upper ring 128 and the lower ring 130 (see FIG. 4). The upper ring 128 and lower ring 130 can be heat sealed together, mechanically coupled, ultrasonically welded or otherwise fixedly associated with one another.

In an alternative embodiment, the upper ring can be omitted. The ostomy bag 106 could be directly coupled to the lower ring 130 using any suitable fixation type. Also, the upper ring 128 has an upper ring body 132 with a collar extension 134, which is optional.

The lower ring 130 can comprise a threaded inner surface 131, which threadably mates with the threaded collar 121 of the annular upper flange 112. In some embodiments, a resilient mechanical detent assembly is formed on a lower end of the lower ring 130. The resilient mechanical detent assembly can comprise a protrusion 136 and actuator 138. When the lower ring 130 is screwed onto the threaded collar 121 of the annular upper flange 112, the protrusion 136 travels along the detent track 126 of the annular upper flange 112 until the protrusion 136 encounters the detent slot 124. The protrusion 136 drops into the detent slot 124, which locks the enterostomy interface 102 to the securement interface 104. That is, the detent slot 124 is connected to an armature 140 that is resiliently biased into an extended position. When the user threads the securement interface 104 onto the enterostomy interface 102, the protrusion 136 contacts the detent track 126, and the armature 140 and protrusion 136 are pivoted upwardly. When the protrusion 136 aligns with the detent slot 124, the armature 140 pushes downwardly due to its resilient biasing, pushing the protrusion 136 into the detent slot 124. The armature 140 is allowed to move downwardly because of the angling of the detent track 126. In some embodiments, the armature 140 has an angled edge 142 that has an angle $A_{AE}$ that is measured relative to a reference plane Rp that is coplanar with a lower surface 143 of the lower ring 130. The armature 140 can fit inside an armature gap 144 fabricated into the sidewall of the annular upper flange 112. The armature gap 144 allows the armature 140 to move up and down as described above. The armature 140 can move upwardly until it contacts an upper surface that defines the armature gap 144. The armature gap 144 includes a space or void near a terminal end of the armature 140 where the protrusion 136 is located. This space or void provides clearance when the armature 140 pivots so that neither the terminal end of the armature 140 or the protrusion 136 interfere with the sidewall of the annular upper flange 112.

When a user desires to remove the ostomy bag 106, the user can pull upward on the actuator 138, which causes the armature to pivot and lift the protrusion 136 from the detent slot 124. When the protrusion 136 is removed from the detent slot 124, the user can rotate the securement interface 104 relative to the enterostomy interface 102 and separate the two.

The lower ring 130 can comprise a threaded inner collar or surface 146 that is configured to engage with the threaded collar 121 of the annular upper flange 112. The lower ring 130 can also comprise a seal groove 148 (see FIG. 14) that is recessed into the internal surface of the lower ring 130. When the lower ring 130 of the securement interface 104 is threaded onto the threaded collar 121 of the annular upper flange 112, the seal, such as an O-ring is compressed between the lower ring 130 and an upper surface of the annular upper flange 112. Stated otherwise, the upper surface of the annular upper flange 112 contacts or mates with the internal surface of the lower ring 130. In sum, the seal can be placed into a seal groove located within a perimeter of an upper surface of the annular upper flange and a similar groove in the lower ring of the securement interface.

Figure 15:
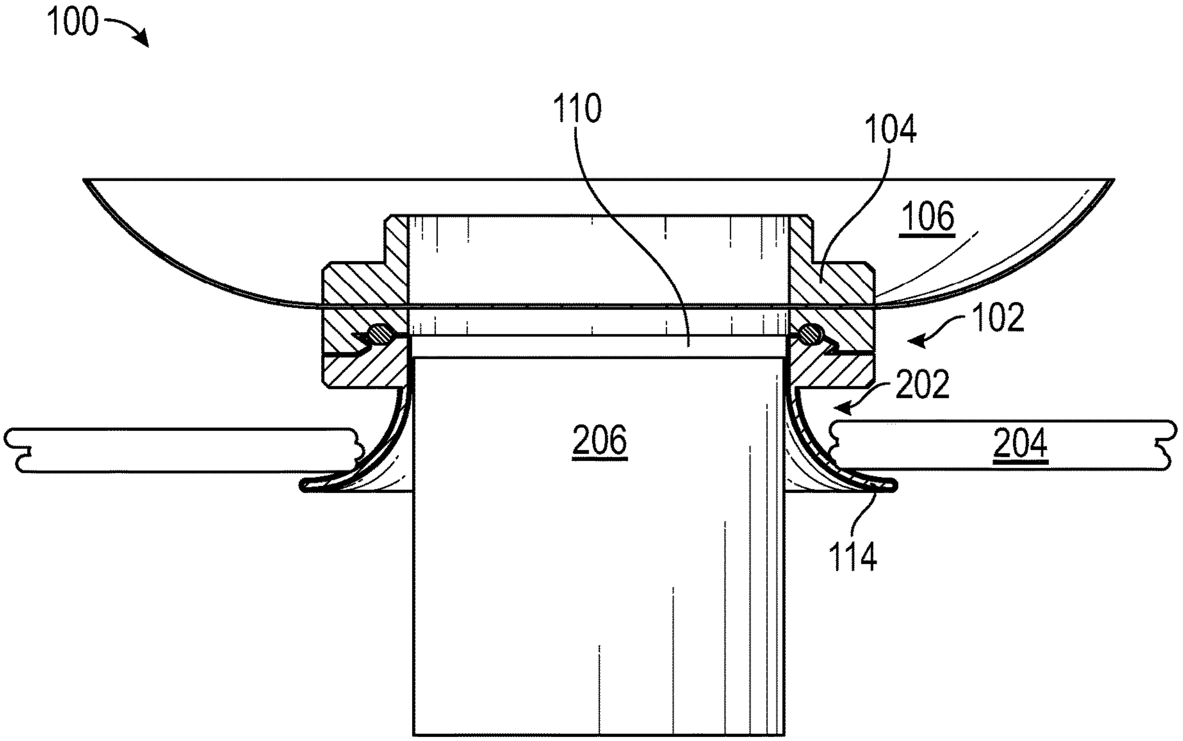
FIG. 15 illustrates an example colostomy apparatus in association with a stoma and bowel of a patient.

FIG. 15 illustrates the apparatus 100 disclosed above in association with a patient. References to FIGS. 1-16 may be made for clarity. The patient has a surgically created stoma 202 in the skin 204 of the abdominal wall. A terminal end 206 of a bowel of the patient, also referred to as the enterostomy, has been pulled through the stoma 202. Rather than suturing the enterostomy directly to the skin 204, the terminal end 206 of the bowel can be sutured to the graft covering 110 that lines the inner surface of the flared lower flange 114. In some instances, the terminal end 206 of the bowel can be sutured to the graft covering 110 prior to inserting the graft into the flared lower flange 114. The flared lower flange 114 of the enterostomy interface 102 can be inserted into the stoma 202. As noted above, the flared lower flange 114 is shaped to reduce a likelihood of the enterostomy interface 102 being pulled out of the stoma 202.

Over time, the bowel/enterostomy will graft onto the graft covering 110. To be sure, the graft covering 110 and the flared lower flange 114 covers the terminal end 206. This both protects the terminal end 206 and also alleviates any discomfort that the patient may incur when visually inspecting the terminal end 206 of the bowel. Thus, the enterostomy interface 102 enhances the patient experience by preserving the dignity of the patient. The securement interface 104 and ostomy bag 106 can then be attached to the enterostomy interface 102.

Any and/or all elements, as disclosed herein, can be formed from a same, structurally continuous piece, such as being unitary, and/or be separately manufactured and/or connected, such as being an assembly and/or modules. Any and/or all elements, as disclosed herein, can be manufactured via any manufacturing processes, whether additive manufacturing, subtractive manufacturing and/or other any other types of manufacturing. For example, some manufacturing processes include three-dimensional (3D) printing, laser cutting, computer numerical control (CNC) routing, milling, pressing, stamping, vacuum forming, hydroforming, injection molding, lithography and/or others.

Any and/or all elements, as disclosed herein, can include, whether partially and/or fully, a solid, including a metal, a mineral, a ceramic, an amorphous solid, such as glass, a glass ceramic, an organic solid, such as wood and/or a polymer, such as rubber, a composite material, a semiconductor, a nano-material, a biomaterial and/or any combinations thereof. Any and/or all elements, as disclosed herein, can include, whether partially and/or fully, a coating, including an informational coating, such as ink, an adhesive coating, a melt-adhesive coating, such as vacuum seal and/or heat seal, a release coating, such as tape liner, a low surface energy coating, an optical coating, such as for tint, color, hue, saturation, tone, shade, transparency, translucency, non-transparency, luminescence, anti-reflection and/or holographic, a photo-sensitive coating, an electronic and/or thermal property coating, such as for passivity, insulation, resistance or conduction, a magnetic coating, a water-resistant and/or waterproof coating, a scent coating and/or any combinations thereof.

The corresponding structures, materials, acts, and equivalents of all means or step plus function elements in the claims below are intended to include any structure, material, or act for performing the function in combination with other claimed elements as specifically claimed. The description of the present technology has been presented for purposes of illustration and description, but is not intended to be exhaustive or limited to the present technology in the form disclosed. Many modifications and variations will be apparent to those of ordinary skill in the art without departing from the scope and spirit of the present technology. Exemplary embodiments were chosen and described in order to best explain the principles of the present technology and its practical application, and to enable others of ordinary skill in the art to understand the present technology for various embodiments with various modifications as are suited to the particular use contemplated.

If any disclosures are incorporated herein by reference and such incorporated disclosures conflict in part and/or in whole with the present disclosure, then to the extent of conflict, and/or broader disclosure, and/or broader definition of terms, the present disclosure controls. If such incorporated disclosures conflict in part and/or in whole with one another, then to the extent of conflict, the later-dated disclosure controls.

The terminology used herein can imply direct or indirect, full or partial, temporary or permanent, immediate or delayed, synchronous or asynchronous, action or inaction. For example, when an element is referred to as being “on,” “connected” or “coupled” to another element, then the element can be directly on, connected or coupled to the other element and/or intervening elements may be present, including indirect and/or direct variants. In contrast, when an element is referred to as being “directly connected” or “directly coupled” to another element, there are no intervening elements present.

Although the terms first, second, etc. may be used herein to describe various elements, components, regions, layers and/or sections, these elements, components, regions, layers and/or sections should not necessarily be limited by such terms. These terms are only used to distinguish one element, component, region, layer or section from another element, component, region, layer or section. Thus, a first element, component, region, layer or section discussed below could be termed a second element, component, region, layer or section without departing from the teachings of the present disclosure.

The terminology used herein is for the purpose of describing particular embodiments only and is not intended to be necessarily limiting of the disclosure. As used herein, the singular forms “a,” “an” and “the” are intended to include the plural forms as well, unless the context clearly indicates otherwise. The terms “comprises,” “includes” and/or “comprising,” “including” when used in this specification, specify the presence of stated features, integers, steps, operations, elements, and/or components, but do not preclude the presence or addition of one or more other features, integers, steps, operations, elements, components, and/or groups thereof.

Example embodiments of the present disclosure are described herein with reference to illustrations of idealized embodiments (and intermediate structures) of the present disclosure. As such, variations from the shapes of the illustrations as a result, for example, of manufacturing techniques and/or tolerances, are to be expected. Thus, the example embodiments of the present disclosure should not be construed as necessarily limited to the particular shapes of regions illustrated herein, but are to include deviations in shapes that result, for example, from manufacturing.

In this description, for purposes of explanation and not limitation, specific details are set forth, such as particular embodiments, procedures, techniques, etc. in order to provide a thorough understanding of the present invention. However, it will be apparent to one skilled in the art that the present invention may be practiced in other embodiments that depart from these specific details.

Reference throughout this specification to “one embodiment” or “an embodiment” means that a particular feature, structure, or characteristic described in connection with the embodiment is included in at least one embodiment of the present invention. Thus, the appearances of the phrases “in one embodiment” or “in an embodiment” or “according to one embodiment” (or other phrases having similar import) at various places throughout this specification are not necessarily all referring to the same embodiment. Furthermore, the particular features, structures, or characteristics may be combined in any suitable manner in one or more embodiments. Furthermore, depending on the context of discussion herein, a singular term may include its plural forms and a plural term may include its singular form. Similarly, a hyphenated term (e.g., “on-demand”) may be occasionally interchangeably used with its non-hyphenated version (e.g., “on demand”), a capitalized entry (e.g., “Software”) may be interchangeably used with its non-capitalized version (e.g., “software”), a plural term may be indicated with or without an apostrophe (e.g., PE’s or PEs), and an italicized term (e.g., “N+1”) may be interchangeably used with its non-italicized version (e.g., “N+1”). Such occasional interchangeable uses shall not be considered inconsistent with each other.

That which is claimed is:

1. An apparatus comprising:

An enterostomy interface that is configured to be partially inserted into a stoma and beneath a skin of a patient, the enterostomy interface comprising:

a flared lower flange that is located at least partially underneath the skin, wherein an enterostomy of the patient is positioned within the enterostomy interface; and an annular upper flange that is located above the skin, such that the skin is located between the flared lower flange and the annular upper flange when the enterostomy interface is inserted into the stoma.

2. The apparatus according to claim 1, further comprising a groove in an upper surface of the annular upper flange.

3. The apparatus according to claim 2, further comprising a seal that is placed into the groove.

4. The apparatus according to claim 1, wherein an ostomy bag is heat sealed between an upper ring and a lower ring of a securement interface that mates with the enterostomy interface.

5. The apparatus according to claim 1, further comprising an ostomy bag having a securement interface that is configured to lockingly mate with the annular upper flange of the enterostomy interface.

6. The apparatus according to claim 5, wherein the annular upper flange is threaded and comprises a detent slot.

7. The apparatus according to claim 6, wherein the securement interface comprises a resilient mechanical detent comprising a protrusion coupled to an actuator, the protrusion drops into a detent slot of the annular upper flange when the lower ring of the securement interface is threadingly engaged with the annular upper flange.

8. The apparatus according to claim 1, further comprising a graft material inserted into the flared lower flange.

* * * * *